United States Patent
Petvai et al.

(10) Patent No.: US 6,475,291 B1
(45) Date of Patent: Nov. 5, 2002

(54) METHOD AND APPARATUS FOR DECOMPOSITION OF SILICON OXIDE LAYERS FOR IMPURITY ANALYSIS OF SILICON WAFERS

(75) Inventors: Steve I. Petvai, Wappingers Falls; Leslie Jane Bohnenkamp, Hopewell Jct., both of NY (US); Michael P. Buet, New Fairfield, CT (US)

(73) Assignee: Beech Grove Technology, Inc., Wappingers Falls, NY (US)

( * ) Notice: Subject to any disclaimer, the term of this patent is extended or adjusted under 35 U.S.C. 154(b) by 0 days.

(21) Appl. No.: 09/557,605

(22) Filed: Apr. 25, 2000

Related U.S. Application Data

(62) Division of application No. 08/968,151, filed on Nov. 17, 1997, now Pat. No. 6,053,984.

(51) Int. Cl.[7] .................................................. C23G 1/02
(52) U.S. Cl. ................................ 134/3; 134/2; 134/30; 134/31; 134/902
(58) Field of Search ........................... 134/2, 3, 10, 11, 134/12, 21, 26, 28, 30, 31, 902, 1.3, 33, 35, 37

(56) References Cited

U.S. PATENT DOCUMENTS

| | | | |
|---|---|---|---|
| 4,990,459 A | 2/1991 | Maeda et al. | 436/178 |
| 5,288,333 A * | 2/1994 | Tanaka et al. | 134/11 |
| 5,395,482 A * | 3/1995 | Onda et al. | 134/1.3 |
| 5,569,328 A | 10/1996 | Petvai et al. | 118/696 |

\* cited by examiner

*Primary Examiner*—Alexander Markoff
(74) *Attorney, Agent, or Firm*—George O. Saile; Stephen B. Ackerman

(57) ABSTRACT

A method and apparatus for decomposing a layer of silicon oxide on a silicon wafer is described which employs the application of a heated mist of aqueous HF to the cooled wafer surface. The technique is applied to the analysis of silicon wafers for trace impurities using a scanning fluid drop to collect the residue containing the impurities after the silicon oxide has been decomposed. The novel method offers an order of magnitude increase in the rate of silicon oxide decomposition over the prior art which uses a vapor phase decomposition technique. In addition the novel method provides better control and safer disposition of the corrosive vapors over the prior art. The apparatus comprises a movable dome fitted with a carrier gas supply and a means for injecting a heated aqueous HF mist generated by a specially designed mist generator into the carrier gas flow. The flow mist droplets are drawn from the flow onto the cooled wafer surface providing a thin layer of liquid aqueous HF which reacts with the oxide layer at a faster rate than previously used HF vapor.

5 Claims, 7 Drawing Sheets

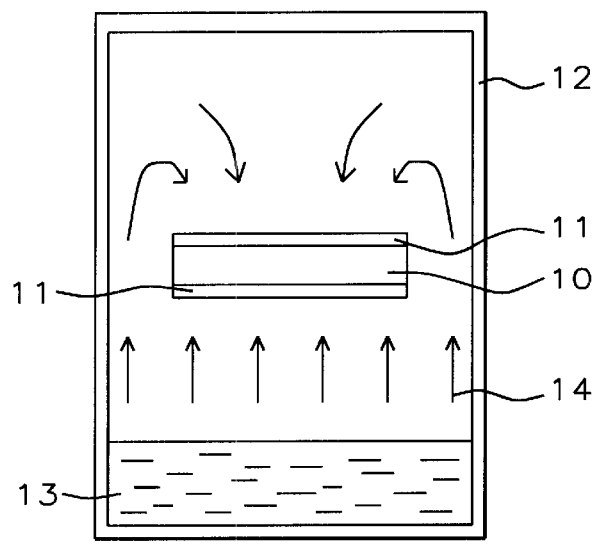
FIG. 1 – Prior Art
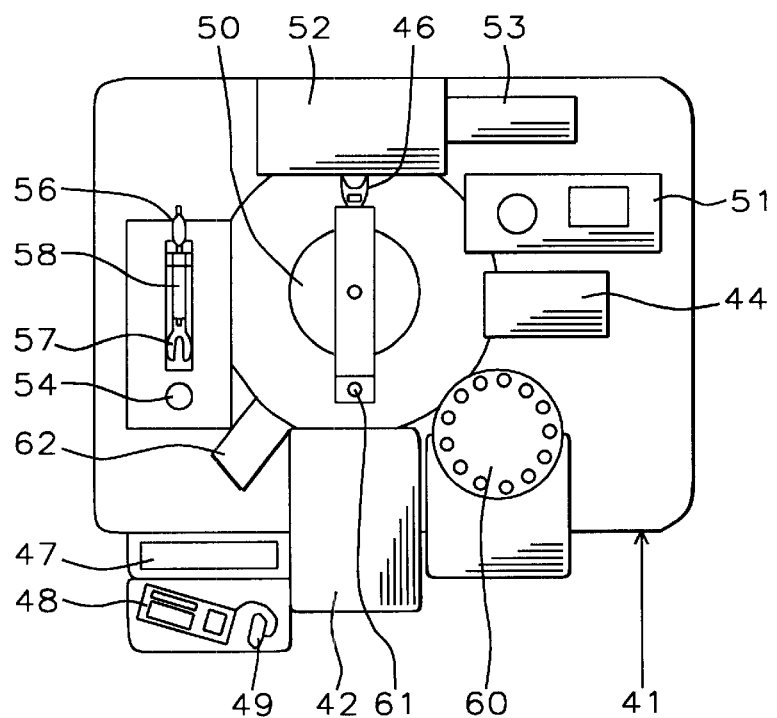
FIG. 2 – Prior Art

US 6,475,291 B1

METHOD AND APPARATUS FOR DECOMPOSITION OF SILICON OXIDE LAYERS FOR IMPURITY ANALYSIS OF SILICON WAFERS

This is a division of Patent Application Ser. No. 08/968,151, filing date Nov. 17, 1997, now U.S. Pat. No. 6,053,984 A Method And Apparatus For Decomposition Of Silicon Oxide Layers For Impurity Analysis Of Silicon Wafers, assigned to the same assignee as the present invention.

BACKGROUND OF THE INVENTION (1) Field of the Invention

The invention relates to processes for the manufacture of semiconductor devices and more particularly to processes related to the analysis of impurities in silicon wafers.

(2) Description of Prior Art

The manufacture of very large scale integrated (VLSI) circuits involves hundreds of discrete processing steps beginning with the introduction of blank silicon wafers. The quality an purity of the starting silicon wafers is, without question, one of the most crucial factors in the performance of the semiconductor devices in the finished product. The current high density, high performance, low cost technology makes widespread use of the metal oxide silicon field effect transistor which depends upon a thin silicon oxide gate insulator. This gate oxide is grown by thermal oxidation of the surface of the silicon wafer.

Trace metallic Impurities within the wafer surface and in the chemicals used to grow layers thereon or to clean or treat oxide layers thereon have a deleterious effect on the performance of the gate oxide as well as on it's reliability. Because of these serious consequences great strides have been taken to provide the highest quality control of the starting material. Additionally, the processing of defective wafers can result in enormous yield losses.

Fortunately, great strides have been by taken by silicon wafer manufacturers to provide reliable substrates. Analytical methods have been found widespread use to properly qualify and characterize silicon wafers. Among these are atomic absorption spectroscopy, emission spectroscopy, inductively coupled mass spectrometry, and X-ray fluorescence.

A well known sampling method which has been developed and cited by Maeda, et. al., U.S. Pat. No. 4,990,459 is a vapor phase decomposition (VPD) technique. The VPD technique extracts and concentrates trace levels of metallic contaminants from the surface of a test wafer by decomposing a layer of silicon oxide with HF vapors. The residue, which contains the non volatile impurities is then collected in a small droplet of a suitable acid such as hydrofluoric acid. The droplet is systematically moved across the entire wafer surface so that all the residue is collected. The recovered droplet is then analyzed by the well known analytical methods mentioned hereinbefore.

Referring to FIG. 1 there is shown a cross section of a prior art sampling technique using VPD, as cited by Maeda et.al. a test wafer 10 having a silicon oxide layer 11 on its surface is placed into a closed chamber 12. A pool of aqueous HF 13, located elsewhere within the chamber 12, emits HF vapors 14 which fill the chamber and, in time, decompose the silicon oxide layer 11. The wafer is then removed and any residue on the polished side of the wafer 10 is collected by a manual method involving the passage of a collection droplet across the wafer surface by tilting the wafer, thereby rolling the drop over the entire surface.

In an earlier patent by the present inventors, Petvai, et.al. U.S. Pat. No. 5,569,328, the sample collection technique was greatly improved by providing automating the movement of the collection droplet. An inert carrier is used to contain the droplet as well as increase the contact area of the droplet. Not only is the reliability and reproducibility of sample collection improved by this apparatus, but the cycle time and the risk of external contamination are greatly reduced. The wafer is mounted on a table having a programmable rotation. The apparatus provides a robotic arm which transports the wafers from a cassette to a VPD chamber where HF vapors decompose the silicon oxide layer. The wafer then passes to the droplet collection station where the sample is collected by a droplet on a pre-loaded sample carrier delivered from a carousel. The entire apparatus operates in an internal class 1 environment.

The long time required to decompose the silicon oxide layer by the use of vapor etching technique illustrated by FIG. 1 affects the cycle time and thereby limits the production capability of the apparatus. This is especially true when thicker, thermally grown, silicon oxide layers are examined. The flash mist method provided by the current invention greatly increases the decomposition rate of the oxide layer.

In order to place the embodiments of this invention into a proper perspective, a brief review of the prominent details of the acid droplet fluid scanner apparatus cited by Petvai, et.al. is now given utilizing FIG. 2 which corresponds to FIG. 4 of that patent.

Wafers, loaded in a cassette, are introduced into the system 41 which encloses a class 1 particle environment, through a small systems interface 42 and placed on cassette stand 44. A pickup fork 46, under robotic control 50 transports a test wafer (not shown) from the cassette stand 44, first to a bar code reader 51 where the wafer is identified, and thence to a VPD etching chamber 52 wherein the silicon oxide layer is decomposed. The robotic arm 50 then delivers the wafer to a rotatable table 54 which is fitted with a vacuum chuck. A translating arm mechanism 58 retrieves a droplet carrier from a carrousel (not shown) and positions the carrier on the fork 57 near the edge of the mounted wafer. A precision liquid handler 61 on the robotic arm 50 retrieves a premeasured volume of liquid and delivers it to the droplet carrier. The wafer table 54 is rotated in a prescribed sequence as the translational arm 58 moves the captured droplet toward the center of the wafer, thereby traversing the entire wafer surface and collecting any residue for the analysis. At the completion of this cycle, the liquid handler 61 retrieves the droplet from the droplet carrier and deposits it back either into a cup in the carousel 60 of an auto sampler, where it is retained for analysis, or onto an inert membrane fitted onto a carrier fixture designed for any of the analytical equipment of choice. The wafer is delivered to the receiving cassette 62. The computer system 47 with accompanying keyboard 48 and mouse 49 are also shown.

SUMMARY OF THE INVENTION

It is an object of this invention to provide an improved method for decomposition of a silicon oxide layer on a silicon wafer which is much faster than prior art methods thus enabling it's usage for real-time production lines.

It is another object of this invention to provide an improved method for decomposition of a silicon oxide layer on a silicon wafer which can be incorporated in a fast cycle time, production capacity, fully automated multi-wafer testing apparatus.

It is yet another object of this invention to provide a method and apparatus for producing ultra clean wafer surfaces as a final step in blank wafer production, and as a surface preparation step for most manufacturing processes in semiconductor manufacturing lines.

It is another object of this invention to describe an efficient and reliable processing station for decomposing a silicon oxide layer on a silicon wafer and collecting an analysis sample of residues by fluid scanning which can be applied as a fast cycle time, production capacity automated wafer testing apparatus.

It is yet another object of this invention to provide a method and apparatus for depositing ultra thin uniform liquid films on flat substrates.

It is yet another object of this invention to provide a method and apparatus for depositing ultra clean thin liquid films, said films being free of all detectable metallic impurities on flat substrates.

These objects and others which will become apparent are accomplished by an apparatus which creates an ultra clean flowing mist of liquid droplets. The mist flow is directed towards the center of a cooled substrate, whereupon it spreads radially over the surface of the substrate. The larger droplets in the stream are drawn to the surface of the cooled substrate by Bernoulli action of the flowing gas.

The deposited liquid layer of aqueous HF reacts with the silicon oxide layer at a much faster rate than the HF vapors used in prior art. As the liquid reacts, the oxide layer is volatilized consuming the aqueous reactant which is continuously being refreshed from the mist stream.

The conditions of the mist application can be controlled by the temperature of the liquid reservoir of the mist generator and the flow rate of the carrier gas. In addition, and unlike the VPD prior art, the mist application can be quickly switched on and off, thereby improving control and reducing purge time. Safety is also improved by improved containment and by way that the flow of corrosive materials may be started and stopped by the operation of a solenoid valve.

BRIEF DESCRIPTION OF THE DRAWINGS

FIG. 1 is a cross sectional view of a prior art method of VPD.

FIG. 2 is a plan view of a prior art automatic fluid scanning apparatus.

DESCRIPTION OF THE PREFERRED EMBODIMENTS

In the embodiments of the current invention the construction of a flash mist chamber and a method for its use in decomposing a layer of silicon oxide on a silicon wafer will be described. Although the apparatus is designed to be used for the preparation of a silicon wafer for sample collection by a fluid scanner, it is not limited to that application. The flash mist chamber is also capable of depositing ultra thin and very clean uniform films of liquids on other substrates. However, in order to provide a proper understanding of the apparatus and of its capabilities it will be described in the context of silicon oxide decomposition for chemical analysis.

The flash mist chamber replaces the VPD sub-station 52 (In FIG. 2). Unlike the prior art apparatus, the $SiO_2$ decomposition step and the fluid scanning operation are performed at the same station, thus eliminating the need to transport the wafer from one station to another. In addition, various other improvements to the overall design and function of the fluid scanner will also become apparent.

Figure 3:
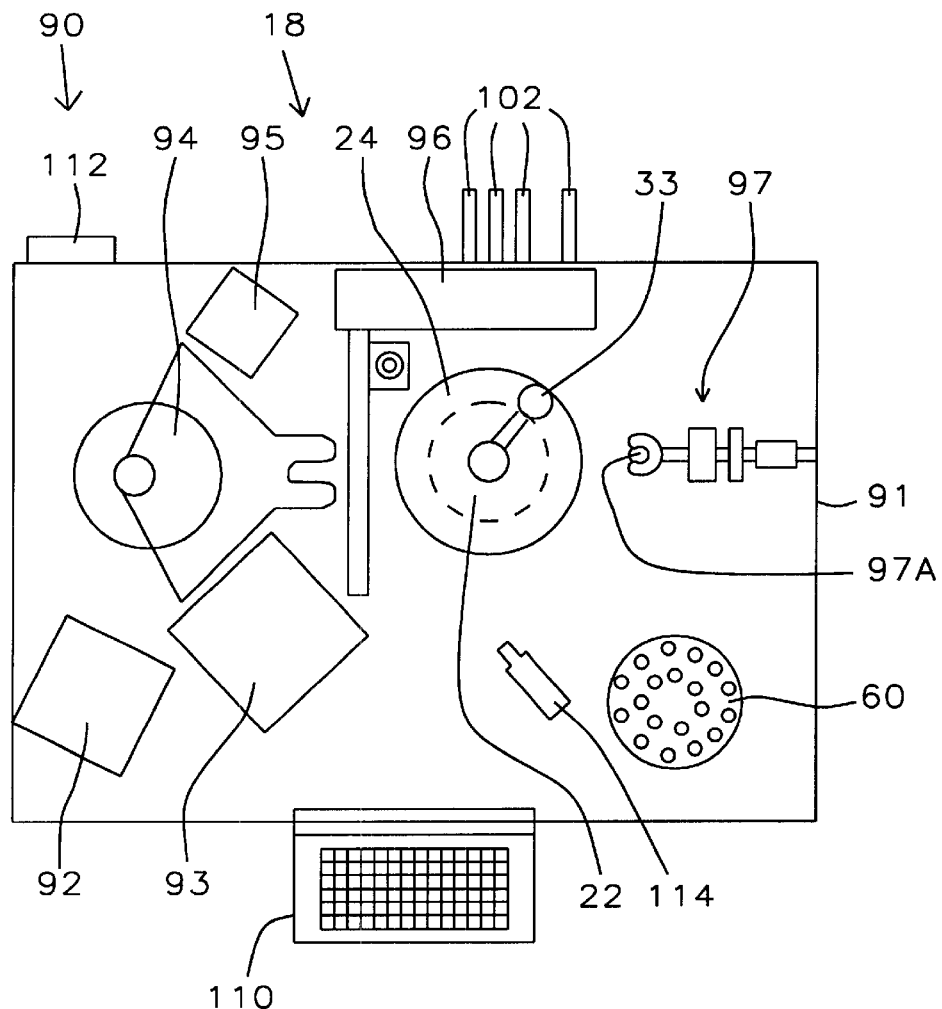
FIG. 3 is a plan view of an automatic fluid scanning apparatus which utilizes the embodiments of the current invention.

FIG. 3 is a plan view of a fully automatic fluid scanner 90 with a wafer processing station 18. Wafer processing station 18 comprises a rotatable table 22 which is serviced by a flash mist chamber 24 which will be hereinafter described, and a translational arm 97 which performs the fluid scan. The various components of the apparatus are housed in an enclosure 91 which provides a class 1 particle environment. The components will be described in the order in which they are employed in the processing of a wafer within the fluid scanner 90. The sequence of steps, performed as a wafer is processed in the fluid scanner, are given in the flow chart of FIG. 10 and are appropriately referenced in the description of the embodiments.

A silicon wafer having a silicon oxide layer over its surface is selected 300(FIG. 10) from input cassette 92 by a robotic wafer handler 94, for example, the Brooks Magnatran 6F wafer transfer robot manufactured by Brooks Automation, Inc., Chelmsford, Mass. (USA). The wafer is presented by the handler 94 to a bar code reader or equivalent 95 where the wafer identification is read and recorded 310(FIG. 10), and thereafter delivered 320(FIG. 10) by the wafer handler 94 to the rotatable table 22. The dome of the flash mist chamber 24, which is a key component of the current invention, is lowered over the wafer 330(FIG. 10) by a pneumatic mechanism(not shown). Decomposition of the $SiO_2$ is then accomplished by the controlled application of a mist containing HF. The operation produces a thin "flash" coating of the liquid etchant on the wafer surface. The mist delivery is maintained until the silicon oxide layer is decomposed and the wafer surface becomes hydrophobic. The chamber 24 is then raised and the surface of the wafer is subjected to droplet scanning by the translational arm 97 which holds a droplet carrier 97A.

The liquid handler 61 on robot arm 50(FIG. 2) is now replaced by a computer interfaced random access auto sampler 96, for example, the Model ASX-510 manufactured by Cetac Technologies, 5600 South 42nd. Street, Omaha, Nebr. (68107), USA. An integrated auto sampler carousel 60, for example, the Model ASX-100 manufactured by Cetac Technologies is provided to manage the droplet samples.

Following the fluid scanning procedure 380(FIG. 10) the wafer is retrieved from table 22 and delivered 400(FIG. 10) to the receiving cassette 93 by the robot wafer handler 94. The collected fluid droplet is delivered 390(FIG. 10) to the carousel 60 for subsequent chemical analysis.

Computer data control is provided through an I/O port 112 and through a keyboard 110. Supply and drain lines 102 provide DI water, vacuum, controlled gas flow, gas exhaust, chemical supply, and drain. A video camera 114 provides remote observation of the droplet collection procedure after the dome assembly 24 is raised, subsequent to the oxide decomposition process. Conventional power supplies, pumps, exhaust gas scrubbers, temperature and gas flow controllers, are located externally to the enclosure 91.

Figure 4:
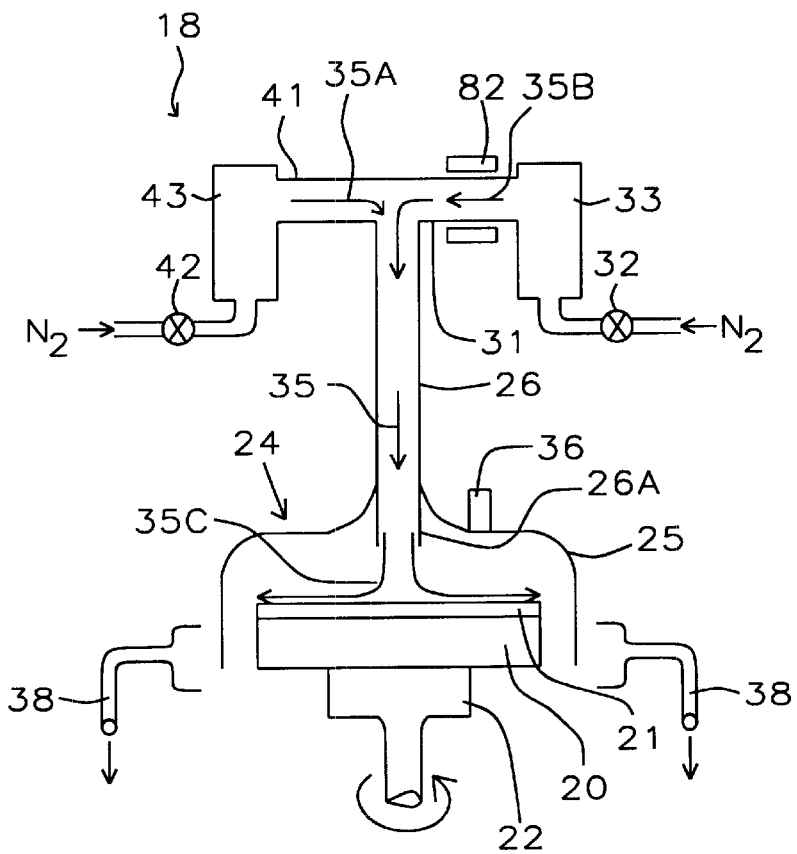
FIG. 4 is a cross sectional view of a first embodiment of the flash mist chamber dome assembly of the current invention.

Referring now to FIG. 4 there is shown a cross sectional view of the essential features of a flash mist chamber 24 engendered in a first embodiment of this invention. A wafer processing station 18 is provided with a rotatable table 22 which is fitted with a vacuum chuck to hold a test wafer 20. The table is fabricated from a chemically resistant material which must also be capable of being machined to a flatness of about 10 microns RMS. A preferred material, which has superior chemical resistance and excellent machinability is "Ultem 2300™", a chemically inert polymer with embedded glass fibers. manufactured by the General Electric Company. The rotation of the table 22 is controlled by a programmable stepping motor(not shown).

A cylindrical dome assembly 24 having a cup shaped portion 25 and an axial tube 26 is located over the wafer 20. The axial tube 26, through which a mist flow is discharged over the wafer 20 has an inside diameter of about ¾ inch and passes through the cup shaped portion 25 of the dome assembly 24 forming an extension 26A within the cup shaped portion 25. The wafer dome assembly 24, table 22, and other components exposed to the corrosive chemicals used in this invention are constructed of a chemically inert material, for example, polypropylene. An infrared temperature sensor 36 is mounted on the dome 25 to monitor the wafer surface temperature. For large diameter wafers, multiple temperature sensors could be fitted on the dome to monitor wafer surface temperature.

A mechanical means, which will be hereinafter described is provided to raise and lower the dome assembly 24 over the wafer 20. The dome assembly 24 is set in a raised position during wafer mount and dismount and during the droplet scanning procedure. FIG. 4 shows the dome assembly in the lowered position wherein the station 18 is configured for the application of a flowing mist which decomposes the silicon oxide layer 21 on the surface of the wafer.

At the upper end of the axial tube portion 26, a side tube 31 connects to a mist generator 33. The mist generator 33 produces a fine mist of liquid droplets of aqueous HF in a nitrogen carrier gas, the size and distribution of which is determined by the operation of the mist generator. A suitable etchant composition contained in the mist generator 33 is a 10:1 dilution of commercially available semiconductor grade 49%HF. The side tube 31 is preferably fitted with a directional microwave source 82 which re-heats the mist entering tube 26 to the proper temperature and also oxidizes trace impurities. Alternatively a resistance heating collar or an rf source may be used to re-heat the mist.

A second mist generator 43 is connected to the column 26 via side tube 41. Mist generator 43 provides a mist of water droplets in a nitrogen carrier gas which is applied prior to the HF decomposition step to cool the wafer surface. Details of the mist generators 33 and 43 will be hereinafter described. Additional mist generators may be added to the dome assembly 18 to permit successive and/or concurrent application of other mist compositions, for example an organic solvent.

The mist flow 35 from either mist generator travels radially across the wafer at a speed determined by carrier gas flow controllers 32,42. The gas mist flow 35C across the wafer 20 creates a low pressure region above the wafer 20 surface due to the Bernoulli effect. This draws the heavier liquid droplets from the flow and onto the surface of the wafer where they adsorb and coalesce over the silicon oxide layer 21.

In operation the wafer surface is initially cooled 340(FIG. 10) by the application of a water mist from mist generator 43. This mist flow 35A cools the wafer surface, largely by evaporative cooling, to a temperature of about 10° C. When this temperature is achieved as indicated by the IR sensor 36, the cooling mist flow 35A is halted and the HF mist flow 35B is begun 350(FIG. 10) from mist generator 33. The deposited liquid layer, now containing HF, reacts with the silicon oxide layer 21, decomposing it by the general reaction:

$$6HF+SiO_2 \rightarrow SiF_6+2H_2O+H_2$$

The dome 25 is designed to distribute the gas flow to provide uniform coverage of the wafer by the depositing liquid film. The products of the reaction are volatile and are taken into the flow, exiting along with undeposited mist, at the edge of the wafer where they are exhausted through receiving channels 38. The receiving channels 38 direct the flow to conventional scrubbers located elsewhere. As can be seen in the figure, the flow stream of the mist mixture is well contained within the system. Thus, under normal operation. the surrounding components of the apparatus are not subjected to the corrosion by escaping fumes. The walls of the dome assembly may also be heated to further prevent contamination of interior dome walls.

The decomposition proceeds until the entire silicon oxide layer 21 has been volatilized, leaving behind a residue containing any non-volatile contaminants which were initially present in the oxide layer. The endpoint of the operation is determined by the onset of hydrophobicity of the wafer surface. The use of a transparent material for the dome assembly 24 or the provision of a window in the dome assembly 24 permits the observation of the wafer surface. However, operation of the station in a production mode usually permits the use of a specified time period to assure completion of the oxide decomposition.

The mist flow for the decomposition process, as determined by the flow controller 32, is experimentally optimized to the chemical exchange rate between the HF and the silicon oxide 21. The deposition rate of the HF mist is between about 1.5 and 2.5 $\mu l/cm^2$/min. and preferably about 2 $\mu l/cm^2$/min.

Upon completion of the oxide decomposition, the mist flow 35B is halted by stopping the flow of nitrogen through the mist generator 33 by the flow controller 32. The remaining mist within the dome area is purged 360(FIG. 10) by re-starting nitrogen flow through mist generator 43. Alternatively and preferably, an separate nitrogen line to the dome assembly 24, independent of the mist generators, may be used to purge the system.The dome assembly 24 is then raised out of the way to allow access of the translational arm of the fluid scanner enabling the fluid droplet sample collection procedure.

Figure 5:
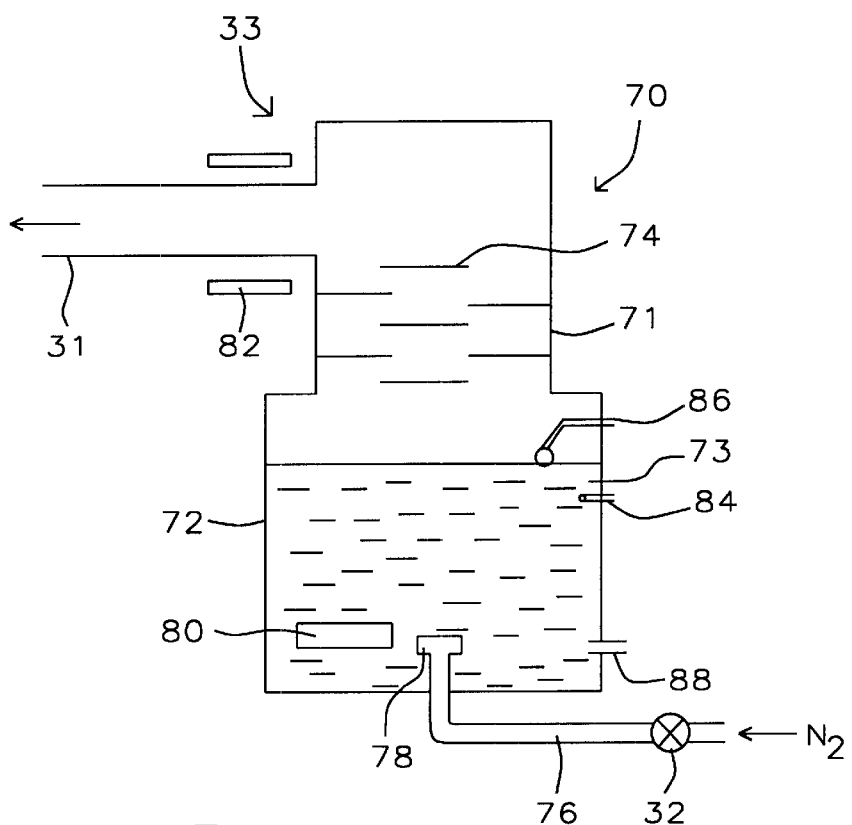
FIG. 5 is a cross sectional view of a mist generator which produces and delivers a heated mist flow the flash mist chamber of this invention.

The mist generator 33 which is an essential part of this embodiment is shown in a detailed cross section in FIG. 5. The body of the generator consists of a lower portion 72 which forms a reservoir for the chemical etchant 73 and an upper portion 71 which contains a system of baffles 74 which return larger liquid droplets to the reservoir and stabilize the mist. The body of the generator 70 is constructed of a chemically inert material such as polypropylene or Teflon™. A gas inlet tube 76 is provided to admit a mist generating and carrier gas, typically nitrogen, into reservoir 72 discharging it though a bubbler 78. Mist particles are formed during the passage of the carrier gas through the liquid chemical etchant 73 which is heated by a resistance heater 80 located within the reservoir 72. The temperature of the chemical etchant in the reservoir is sensed by a thermocouple 84 within the liquid 73, which controls the operation of the resistance heater 80.

Optionally, a fluid level sensor 86 may be provided to signal an external etchant supply to dispense etchant through inlet 88, whereby a constant level of liquid may be maintained within the generator. The droplet size distribution and mist concentration in the output stream are controlled by the temperature of the liquid 73 in the reservoir, the nitrogen flow rate, and by the system of baffles 74. Larger droplets in the mist stream are returned to the reservoir by the baffles 74. The arrangement of the baffles 74 must be determined experimentally in order to accomplish the desired droplet size of the mist stream exiting the bubbler. A preferred droplet diameter in the current application is 10 microns or thereabout.

A directional microwave source 82 at the mist generator discharge tube 31 is used to re-heat the mist droplets which have cooled in their travel through the baffles of the mist generator. A commercially available microwave source having a capacity of about 10 watts is suitable for this application. The application of microwave energy to re-heat the mist droplets has the added advantage of elimination of trace metallic impurities from the mist. Re-heating of the mist ensures the proper temperature differential between the mist and the wafer surface upon which deposition takes place. This temperature differential is critical to the speed of the process, but not to the process itself. The preferred mist temperature is 40° C. or thereabout and a temperature differential of 30° C. or thereabout.

Alternatively, re-heating may be accomplished with a resistance heater wrapped around the output tube 31 of the mist generator in place of the microwave source 82, however, the benefits of microwave mist purification are sacrificed. An rf coil surrounding the discharge tube 31 may also be used.

Mist generator 43(FIG. 4) is basically identical to mist generator 33 with the exception that water is contained in its reservoir and mist heating is not required.

Figure 6:
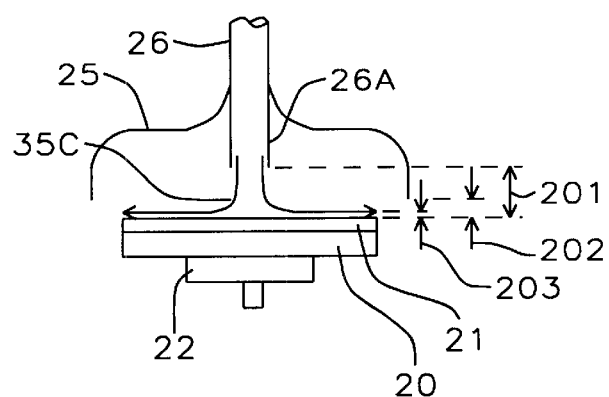
FIG. 6 is a cross sectional view of a portion dome assembly of the current invention showing critical dimensions for maintaining mist flow

FIG. 6 shows is a cross section of the lower portion of the dome assembly in the lowered position showing the dimensions which are critical to maintaining proper laminar flow and a uniform steady state liquid deposition over the wafer. The opening of the axial tube 26A from which the mist flow is discharged over the wafer 20 is between about 1 and 4 inches above the wafer surface 201. The lower lip of the dome assembly 25 is between about 0.5 and 1.0 cm above the plane of the wafer surface 202. The base of the mist laminar flow region is less than about 1 mm above the wafer surface 203.

Figure 7:
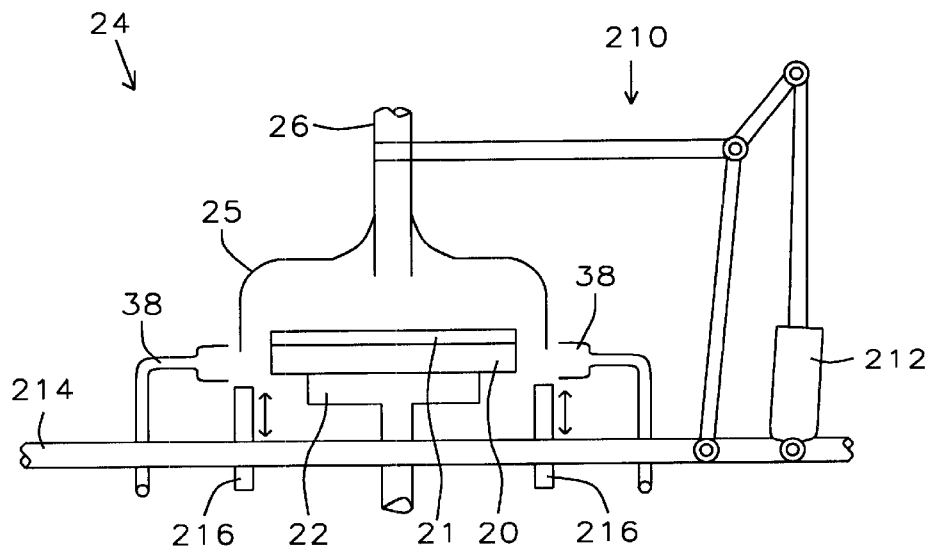
FIG. 7 is a cross sectional view of the dome assembly of the current invention including the dome lifting mechanism in the lowered position during the mist application step.

FIG. 7 is a cross section showing the dome assembly in the lowered position over the mounted wafer 20 and illustrating the pivoted raising/lowering mechanism 210 which is operated by a computer controlled pneumatic cylinder 212 and anchored on the base plate 214 of the system enclosure. two pneumatically operated guide pins 216 located below the lower lip of the dome 25 are in a raised position as the dome assembly 24 is lowered into position over the wafer. They serve to bring the dome to rest at the proper spacings as illustrated in FIG. 6 and concentric with the wafer edge. After the dome has come to rest, the pins 216 are retracted so as not to disrupt the mist flow during the flash mist application.

Figure 8:
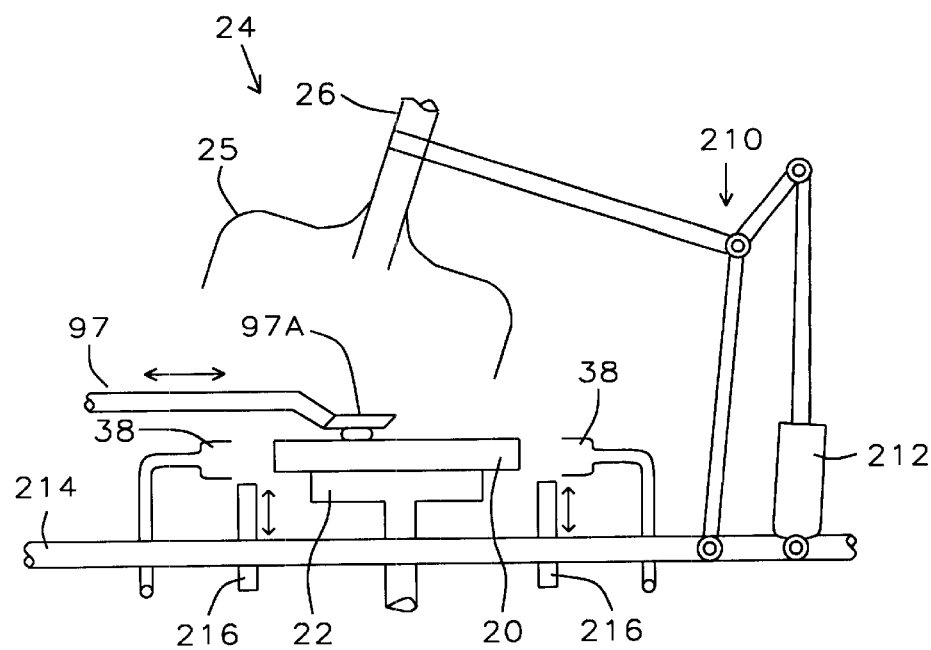
FIG. 8 is a cross sectional view of the dome assembly of the current invention including the dome lifting mechanism in the raised position during the droplet scanning step.
Figure 10:
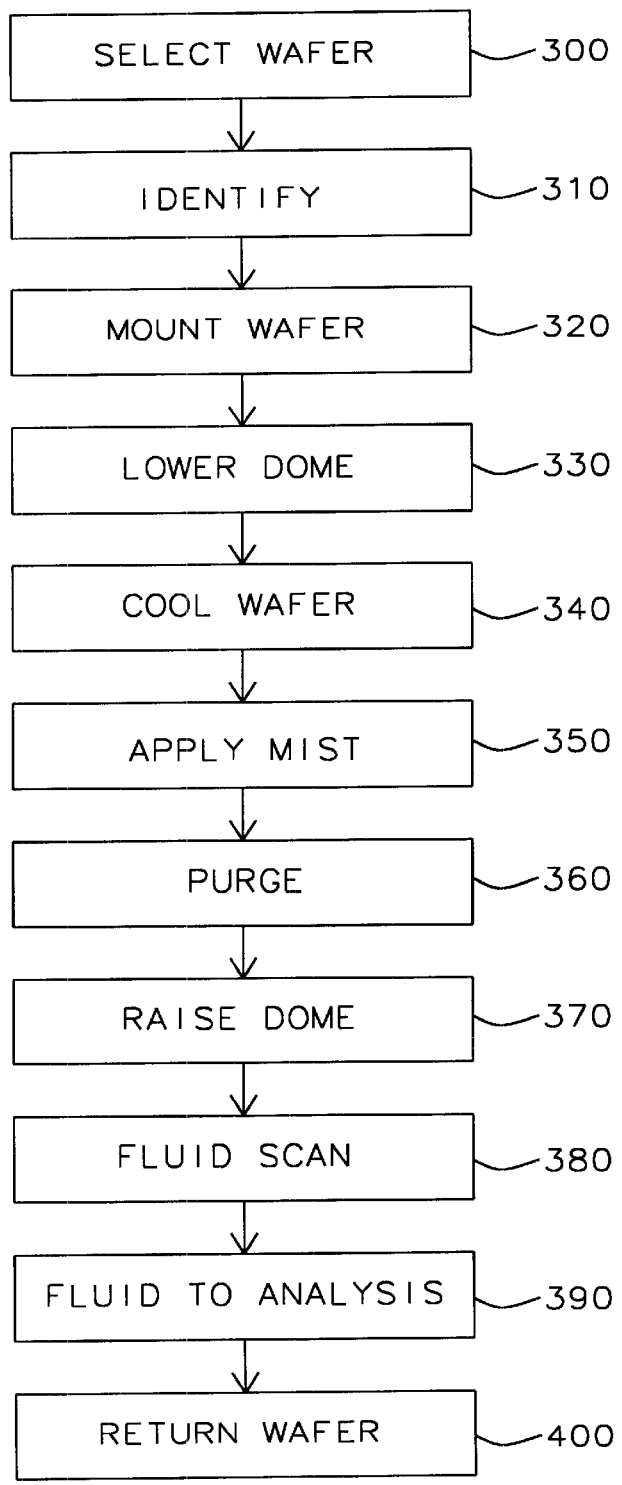
FIG. 10 is a flow chart illustrating the steps used in processing a wafer with the apparatus described by this invention.

FIG. 8 is a cross section showing the dome assembly 24 in the raised position as it appears during the fluid scanning operation 380(FIG. 10). The translational arm 97 with the fluid droplet carrier 97A is shown extended over the wafer 20 as it performs a surface scan.

In a second embodiment of the invention a flash mist assembly is described which uses a vortex tube instead of a water droplet mist to provide cooling of the wafer surface prior to the application of the silicon oxide decomposing HF mist. The vortex tube was developed in 1930 by the French physicist George Ranque. A compressed gas is cause to flow in a spiral pattern in a tube forming a vortex. Upon reaching the end of the tube. some of the flow exits the tube and some is forced back, passing through the center of the vortex at a lower speed. Heat exchange takes place between the slower and faster moving streams, thereby causing cooler gas to emit from one end of the tube. By directing a flow of nitrogen cooled by a vortex tube at the wafer, the surface may be cooled to proper temperature in less than 10 seconds.

Figure 9:
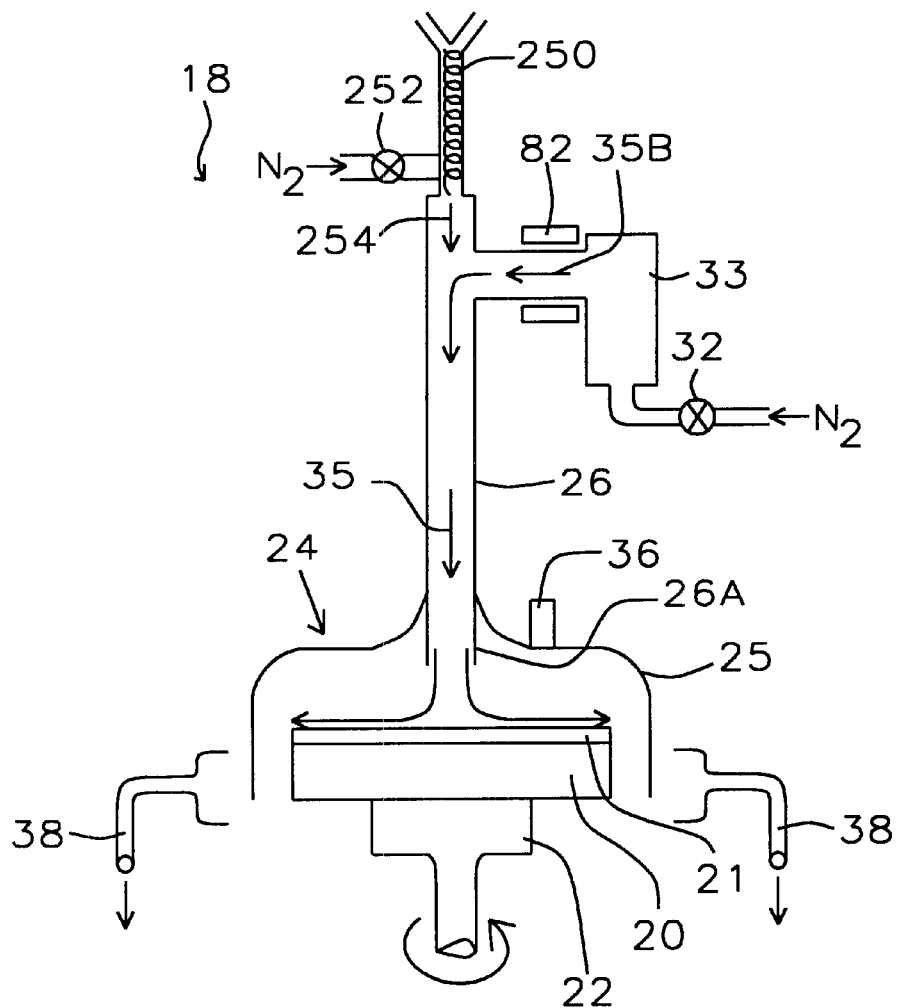
FIG. 9 is a cross sectional view of a second embodiment of the flash mist chamber dome assembly of the current invention.

Referring to FIG. 9, there is shown a flash mist dome assembly which has a vortex tube 250 fitted to the end of tube 26. Nitrogen is admitted by flow controller 252 and cooled by the action of the vortex tube 250 emitting a cooled nitrogen flow 254 towards the wafer 20. Other components of the dome assembly are identical to those of the first embodiment.

Vortex tubes are commercially available in many capacities from the Vortec Corporation, 3770 Ridge Pike, Collegeville, Pa. 19426. A unit having a rating of 8 SCFM or thereabout is suitable for cooling a wafer for flash mist application of the current invention.

The operation of flash mist oxide decomposition station will now be described with reference to FIGS. 5, 7, 9, and 10. With the dome assembly 24 in the raised position, the test wafer is placed on the rotatable table 22 by the handler 94 Vacuum is applied to the chuck and a slow table rotation is begun. The dome assembly 24 is lowered by the pneumatic cylinder 212 over the wafer to the specified dome-to-wafer spacing, and the stop pins 216 are retracted.

A nitrogen flow 254 is begun though the vortex tube 250 by activating the flow controller 252. The flow is maintained for about 15 seconds thereby cooling the wafer surface 340(FIG. 10) to a temperature of between about 5° C. and 20° C. and preferably at 10° C. or thereabout whereupon the nitrogen flow through the vortex tube 250 is shut off. Meanwhile the fluid reservoir of the mist generator 33 is filled to a working level with an aqueous HF solution, for example a 10% HF/H2O solution. The heater 80 is activated and the temperature of the HF solution is raise to a temperature of 40° C. or thereabout.

The solenoid valve 32 next opened causing nitrogen to flow through the bubbler 78. of mist generator 33. A mist flow begins above the reservoir and is stabilized by the baffles 74. The stabilized mist flow is then introduced into the axial tube 26 passing through the field of the microwave source 82 wherein the mist is heated to a temperature of between about 30° C. and 40° C. The microwave unit also eliminates trace metallic impurities from the mist flow. The mist flow is maintained for a period of time sufficient to decompose the entire silicon oxide layer 350(FIG. 10). Under the conditions cited in this embodiment, the rate of removal of the silicon oxide layer is approximately 100 Å/minute. In the prior art VPD technique a 360 Angstrom silicon oxide layer requires 5 minutes for complete decomposition. Using the application of acid mist according to the current invention the same layer can be decomposed in approximately 15 seconds.

When the silicon oxide decomposition has been completed, the mist flow is stopped by the closure of solenoid valve 32. Nitrogen is then flowed through the dome assembly 24 for a period of 5 seconds or thereabout to purge the assembly of etchant vapors 360(FIG. 10). The dome assembly 24 is then raised 370(FIG. 10) to provide access to the wafer by the translational arm 97 which collects the residue sample from the wafer 20 by scanning the wafer surface with a liquid acid droplet supported in the carrier 97A. The subsequent steps including the scanning droplet sample collection step 380(FIG. 10) and the return of the wafer to a receiving cassette for further processing 400(FIG. 10) are well known and are discussed in detail in the references.

The dome assembly with the attached mist generator with wafer cooling by either water mist as in the first embodiment or by vortex tube as in the second embodiment may be used separately from the fluid scanner apparatus for the deposition of other liquids onto substrate surfaces. The apparatus may be used to deposit thin uniform liquid layers onto substrates where such layers may be required. The extraordinary control of the mist/gas mixture attainable by the current apparatus is due in large part by the capability of instantaneous reheating of the mist at the generator discharge. Re-heating at this point provides excellent control of the temperature differential between the mist and the substrate upon which deposition takes place. The temperature differential is critical to the speed of the process, but not the to the process itself.

The flash mist process of this invention permits the rapid decomposition and volatilization of silicon oxide films having thicknesses several microns thick. The depth of penetration of a thick oxide layer is operator controlled.

Whereas the embodiments of this invention illustrate the use of HF for the decomposition of silicon oxide films, the apparatus and method taught is not limited to this application. Other materials may similarly be controllably volatilized by other etchants where such volatilization is possible.

While this invention has been particularly shown and described with reference to the preferred embodiments thereof, it will be understood by those skilled in the art that various changes in form and details may be made without departing from the spirit and scope of the invention.

What is claimed is:

1. A method for forming a liquid film over a substrate by application of a mist comprising:
    (a) providing a substrate;
    (b) providing an apparatus having;
        (i) a rotatable table for supporting said substrate;
        (ii) means for cooling said substrate;
        (iii) a cylindrical dome assembly positioned over said table;
        (iv) means for raising and lowering said dome assembly;
        (v) means for introducing a heated mist flow into said dome assembly;
        (vi) means for heating said mist flow;
        (vii) means for recovery and disposition of exhaust gases;
    (c) mounting said substrate on said table;
    (d) lowering said dome assembly over said substrate;
    (e) rotating said table;
    (f) cooling said substrate;
    (g) introducing a mist flow into said dome assembly;
    (h) maintaining said mist flow for a time period thereby forming said liquid film; and
    (i) halting said mist flow.

2. The method of claim 1 wherein said liquid film is selected from the group consisting of an acid, a solvent, a lubricant, a monomer, and water.

3. The method of claim 1 wherein said table is rotated during said cooling and said introducing and said maintaining of said mist flow.

4. The method of claim 1 wherein said substrate is cooled to a temperature between about 5° C. and 15° C.

5. The method of claim 1 wherein said the mist flow is heated to between about 30° C. and 40° C.

* * * * *